US006622045B2

(12) United States Patent
Snell et al.

(10) Patent No.: US 6,622,045 B2
(45) Date of Patent: Sep. 16, 2003

(54) SYSTEM AND METHOD FOR REMOTE PROGRAMMING OF IMPLANTABLE CARDIAC STIMULATION DEVICES

(75) Inventors: Jeffery D. Snell, Chatsworth, CA (US); John W. Poore, South Pasadena, CA (US); Jason A. Sholder, Hartford, CT (US)

(73) Assignee: Pacesetter, Inc., Sylmar, CA (US)

( * ) Notice: Subject to any disclaimer, the term of this patent is extended or adjusted under 35 U.S.C. 154(b) by 338 days.

(21) Appl. No.: 09/823,374

(22) Filed: Mar. 29, 2001

(65) Prior Publication Data

US 2002/0143372 A1 Oct. 3, 2002

(51) Int. Cl.$^7$ ................................................ A61N 1/08
(52) U.S. Cl. .............................. 607/30; 607/32; 607/59; 607/60
(58) Field of Search ................................ 607/4, 5, 7, 9, 607/10, 30, 31, 32, 59, 60, 17, 18; 128/903

(56) References Cited

U.S. PATENT DOCUMENTS

| | | | | |
|---|---|---|---|---|
| 4,388,929 A | * | 6/1983 | Renirie et al. ................ 607/30 |
| 5,243,977 A | * | 9/1993 | Trabucco et al. ............. 607/10 |
| 5,383,915 A | | 1/1995 | Adams ........................ 607/60 |
| 5,433,736 A | | 7/1995 | Nilsson ....................... 607/59 |
| 5,456,692 A | | 10/1995 | Smith, Jr. et al. ............. 607/31 |
| 5,690,690 A | * | 11/1997 | Nappholz et al. ............. 607/30 |
| 5,725,559 A | | 3/1998 | Alt et al. ...................... 607/5 |
| 5,752,976 A | | 5/1998 | Duffin et al. ................. 607/32 |
| 5,836,987 A | * | 11/1998 | Baumann et al. ............. 607/17 |
| 6,073,049 A | * | 6/2000 | Alt et al. ..................... 607/31 |

* cited by examiner

Primary Examiner—Willis R. Wolfe

(57) ABSTRACT

To permit remote programming of implantable cardiac stimulation devices such as pacemakers, a central device programmer is provided in conjunction with a network of remote telemetry units for use in patient homes or in remote clinics. To reprogram a device implanted within a patient, a physician enters programming commands within the central programmer which relays the programming commands to a remote telemetry unit in proximity to the patient. The remote telemetry unit, in turn, forwards the programming commands to the implanted device. In this manner, the patient need not return to the physician for reprogramming of the device. Remote telemetry units may be provided within patient homes, clinics, hospital emergency rooms, hospital patient rooms, and the like. Depending upon the implementation, different levels of programmability may be permitted depending upon the degree of supervision of the patient. For an unsupervised patient, limited programmability is permitted. For a nurse-supervised patient, a greater degree of programmability is permitted. Finally, for a physician-supervised patient, a full range of programmability is permitted. In a specific example described herein, each remote telemetry unit includes minimal hardware and software components necessary to relay programming commands, diagnostic information, and other signals between the central programmer and the implanted device.

32 Claims, 5 Drawing Sheets

SYSTEM AND METHOD FOR REMOTE PROGRAMMING OF IMPLANTABLE CARDIAC STIMULATION DEVICES

FIELD OF THE INVENTION

The invention generally relates to external programmers for use with implantable cardiac stimulation devices and to methods for programming implantable cardiac stimulation devices.

BACKGROUND OF THE INVENTION

A wide range of implantable cardiac stimulation devices are provided for surgical implantation into humans or animals. One common example is the cardiac pacemaker. Another is the implantable cardioverter defibrillator (ICD). Other examples include devices for stimulating or sensing portions of the brain, spinal cord, muscles, bones, nerves, glands or other body organs or tissues. Another example is an implantable drug pump.

Implantable cardiac stimulation devices, particularly pacemakers, are often configured to be used in conjunction with an programmer which allows a physician to program the operation of the device to, for example, control the specific parameters by which the device detects arrhythmia conditions and responds thereto. For instance, the programmer may allow the physician to specify the sensitivity with which the device senses electrical signals within the heart and to further specify the amount of electrical energy to be employed for pacing the heart in circumstances where expected heart signals are not sensed. Additionally, the programmer may be configured to receive and display a wide variety of diagnostic information detected by the device, such as graphs of electrical heart signals sensed by the device and responsive pacing signals. Also, the programmer may operate to analyze the data received from the device to assist the physician in rendering diagnoses as to possible arrhythmias and to assist the physician in programming the device to provide appropriate therapy.

Current state of the art implantable cardiac stimulation devices may have dozens or hundreds of programmable parameters that can be individually programmed using the external programmer. The programmable parameters permit the operation of the cardiac stimulation device to be tailored to the needs of the particular patient to provide optimal therapy while minimizing the risk of any unnecessary therapy. Unfortunately, it is often difficult to predict what the resultant operation will be for any given patient with any selected set of parameter settings. Hence, a potentially viable set of parameters is chosen by the physician, the implantable cardiac stimulation device is programmed using the selected set of parameters, and then the patient is sent home. Weeks or months later the patient must return to the physician's office for a follow-up appointment so that they physician may evaluate the results of the selected parameters. Typically, the follow-up evaluation consists of the physician making judgments based upon observing several characteristics of the patient and of the implanted cardiac stimulation device. If the device is a pacemaker, the physician typically reviews intracardiac electrogram (IEGM) data recorded by the cardiac stimulation device and also reviews information pertaining to the present operating status of the device via telemetric interrogation of diagnostic data stored within the device. The diagnostic data may, for example, specify the operation of the device over a prior recording period, such as over the last few weeks or months. Specific types of diagnostic information that may be provided includes information identifying the percentage of paced versus sensed beats, heart rate histograms, sensor rate histograms, etc. Additional diagnostic information specifies the battery voltage, lead impedance, etc. of the device. The physician collates the information and makes adjustments to the programming of the device. Again, the patient is sent home for several more weeks or months until another follow-up visit. This cycle may be repeated numerous times before optimal device settings are determined by the physician.

As can be appreciated, it would be highly desirable to limit the need for patients to return to the physician for follow-up sessions, to thereby reduce the cost and inconvenience to the patient and to permit the physician to devote a greater amount of time to the more urgent needs of other patients. One solution that has been proposed is to provide the patient with a telemetry device for receiving programming commands via telephone from a programmer maintained by the physician and for relaying programming commands to the implantable cardiac stimulation device within the patient via remote telemetry. In this manner, the physician can reprogram the implantable cardiac stimulation device without requiring the patient to return to the physician's office.

One concern with the proposed system is that, if the remote device is operated only under the control of the patient, incomplete or improper programming of the implanted device may occur. In this regard, patients with implanted cardiac stimulation devices are often elderly and, in at least some cases, are not able to reliably position a hand-held telemetry unit of the remote device in proximity to the implanted device throughout an entire reprogramming session. As a result, only a portion of reprogramming commands transmitted from a central programmer may be received by the implanted device, possibly resulting in improper programming of the device. Depending upon the parameters being reprogrammed, the improper reprogramming may result in significant changes in the operation of the implanted device, perhaps resulting in a loss of consciousness of the patient. As can be appreciated, if the patient is at home and unattended by a nurse or physician, it may be necessary to send an ambulance to the home of the patient to revive the patient. However, if the remote programming device is installed within a nursing clinic, hospital emergency room, or the like, where the remote programming unit may be operated under the control of a nurse or other medical professional, the aforementioned concerns are not an issue. Accordingly, it would be highly desirable to provide a remote programming system which controls the type of reprogramming permitted using a remote programming device based upon the degree of supervision of the patient and it is to that end that aspects of the invention are directed.

Another concern with the proposed remote programming system is that the cost of the remote unit may be quite high, thus discouraging physicians from providing the remote programmers to their patients or discouraging insurance companies from paying for the remote programmers. For example, one specific proposed remote programming system for use by an patient (discussed in U.S. Pat. No. 5,752,976) includes a wireless or cellular telephone and a geosynchronous positioning system (GPS) transceiver. The wireless or cellular telephone permits the patient to converse with the physician and also to receive and transmit programming commands, diagnostic information and the like. The GPS system permits the location of the patient to be determined, particularly if the patient is unable to respond to telephonic requests by the physician. Although the system permits remote reprogramming of the implantable cardiac stimulation device, the inclusion of a wireless telephone and GPS system may render the remote system quite expensive, and thereby only appropriate for certain high risk patients. Accordingly, it also would be desirable to provide an remote programming system which is relatively inexpensive to thereby permit most or all patients to receive the benefits of remote programming and it is to this end that others aspects of the invention are directed.

SUMMARY OF THE INVENTION

In accordance with the invention, a system is provided for remote programming of an implantable cardiac stimulation device implanted within a patient. The system includes a central programmer device operative to generate and transmit programming signals for use in programming a stimulation device implanted within a patient. The programming signals are generated, in part, based upon a degree of direct medical supervision of the patient during programming of the device. A remote programmer device is provided for use in proximity to the patient a remote programmer device. The remote programmer device is operative to receive and relay the programming signals transmitted by the central programmer device to the stimulation device of the patient to program the stimulation device with the programming signals.

In an exemplary embodiment, the implantable cardiac stimulation device is a pacemaker or ICD. The degree of supervision is either supervised or unsupervised. If unsupervised, remote programming of only non-life-threatening functions is permitted, such as programming of diagnostic functions, sleep mode functions, and the like. Programming of other functions, such as sensitivity parameters, pacing mode parameters, is not permitted or, if permitted, is restricted to particular ranges of programming values. If the patient is supervised, however, a full range of programming parameters and values is permitted. Depending upon the implementation, the indication of the degree of supervision may be manually entered into the central programmer by the physician or automatically determined by querying the remote device. Additional levels of supervision maybe accommodated as well, such as physician-supervised, nurse-supervised or unsupervised. By controlling the generation of programming signals based on the degree of supervision of the patient, the risk of improper or incomplete programming of critical parameters of the implanted device is substantially avoided.

Also, in the exemplary embodiment, the remote programmer device includes only those components necessary to relay programming signals and diagnostic information between the central programming device and the implantable cardiac stimulation device such that the costs associated with the remote programmer device are minimal.

In another exemplary embodiment, the remote programmer additionally includes a Holter monitor for detecting and recording surface electrocardiogram (ECG) signals. The remote device additionally includes a modular memory unit for storing the recorded signals. The modular memory unit also stores control software for controlling the operations of the remote programmer permitting the remote programmer to be easily upgraded to operate in conjunction new or modified implanted devices.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE PREFERRED EMBODIMENTS

The invention relates to improved techniques for programming implantable medical devices. The invention will be described primarily with reference to a pacemaker used in conjunction with an external programmer device, but principles of the invention are applicable to other implantable medical devices such as ICDs and to other external control devices as well.

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
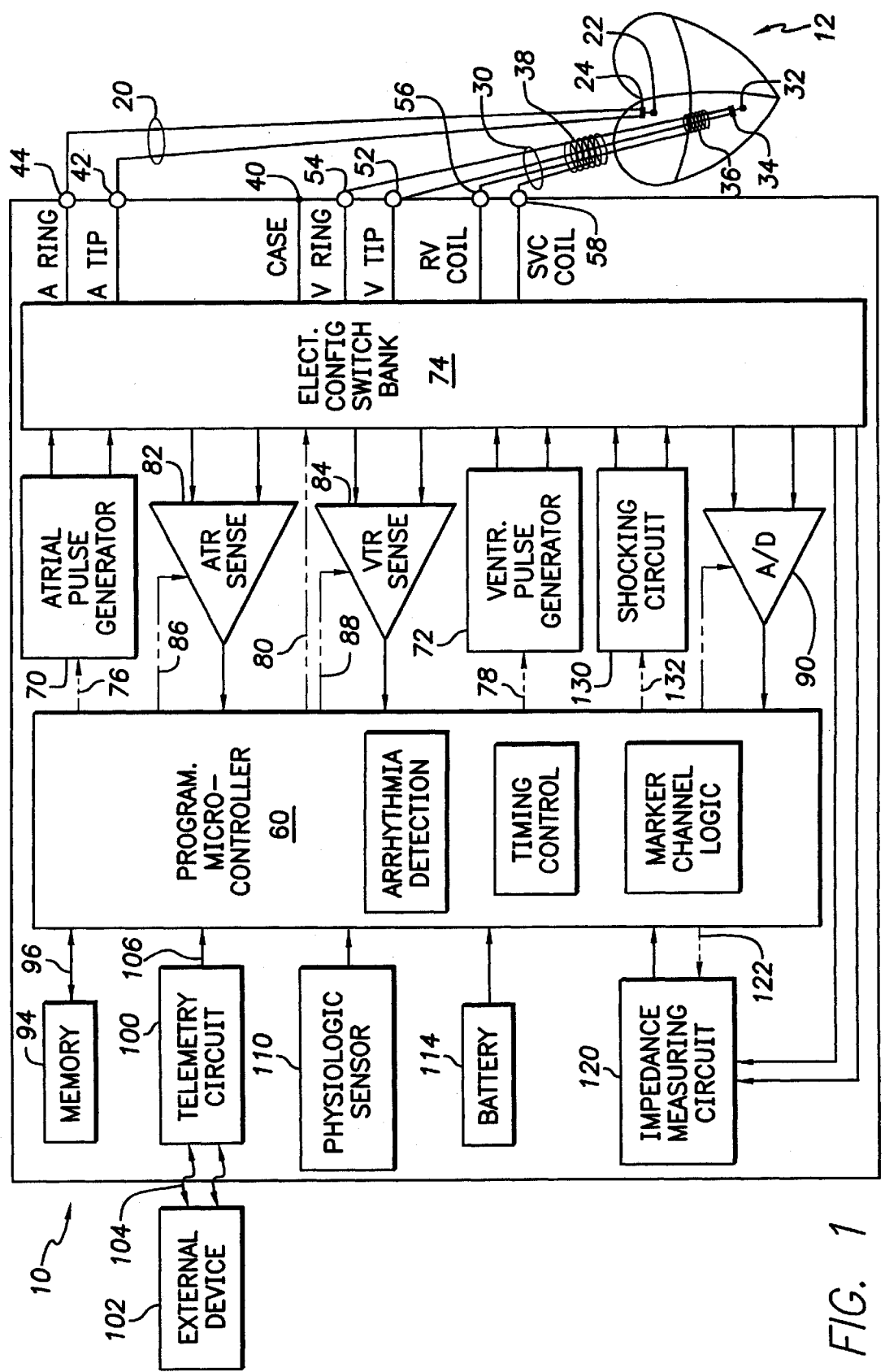
FIG. 1 is a functional block diagram of a dual-chamber implantable stimulation device illustrating the basic elements of a stimulation device which can provide cardioversion, defibrillation and pacing stimulation in accordance with an exemplary embodiment of the invention.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation or to add or enable appropriate circuitry to provide a multiple chamber stimulation device capable of treating all four chambers of the heart or otherwise capable of treating multiple sites about the heart.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the various coil electrodes. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM and/or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses, that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power amplifier with programmable gain adjusted by microcontroller 60 via gain control signals 86 and 88, respectively, and/or with automatic gain control, band pass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the or time atrial and ventricular pulse generators, 70 and 72, respectively, in a demand fashion whenever cardiac activity is sensed in the respective chambers. For arrhythmia detection, the present device utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of a normal rhythm of an arrhythmia. The timing intervals between sensed events (e.g., the P-P, P-R, R-P, and R-R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time, and then, if the device is an ICD, must also be capable of providing high-current pulses (for capacitor charging) when the patient requires a shock pulse. The battery 114 must also have a predictable discharge characteristic so that elective replacement time can be detected. Accordingly, the device employs lithium/silver vanadium oxide batteries, as is true for most (if not all) such ICD devices to date.

It is the primary function of the invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level, are synchronized with an R-wave, and pertain to the treatment of an atrial arrhythmia. Defibrillation shocks are generally of moderate to high energy level (i.e., corresponding to thresholds in the range of 5–40 Joules), delivered asynchronously (since R-waves may be too disorganized), and pertaining exclusively to the treatment of ventricular arrhythmia. Accordingly, the microcontroller 60 is capable of controlling the synchronous or asynchronous delivery of the shocking pulses.

Figure 2:
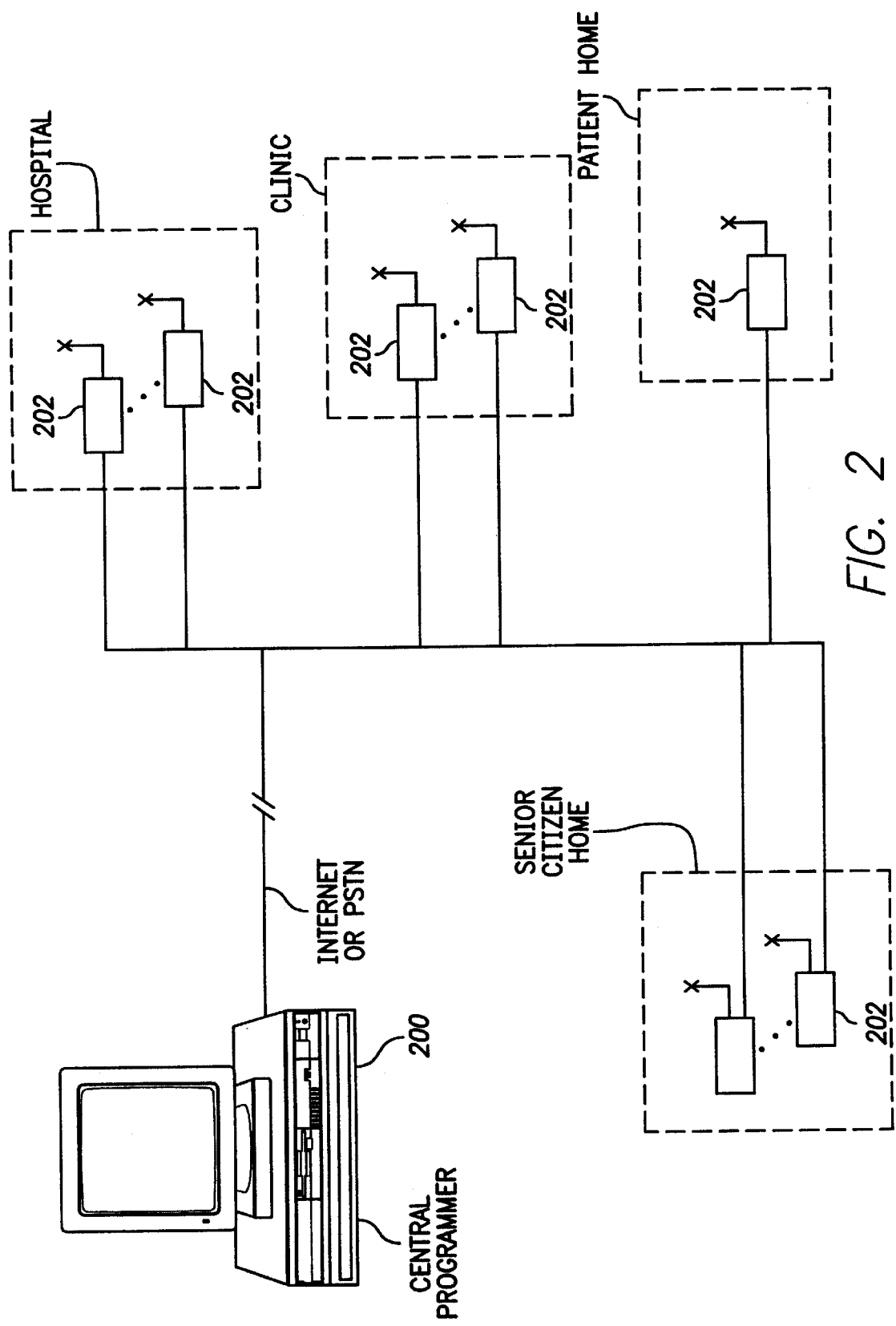
FIG. 2 is a block diagram of a central programmer and a distributed network of remote telemetry units for use in programming implantable cardiac stimulation devices of the type illustrated in FIG. 1.

FIG. 2 illustrates a system for programming an implanted cardiac stimulation device such as the device of FIG. 1. A central programmer 200 is provided for use with a distributed network of remote telemetry units 202 installed within hospitals, clinics, or patient homes. The central programmer is a full-function programming unit capable of programming all functions of the implanted cardiac stimulation device and capable of displaying diagnostic information received from the implanted device. The central programmer may be a dedicated programmer unit or a personal computer (PC) provided with necessary software and hardware for performing implanted device programming functions. The remote telemetry units are preferably provided with only sufficient hardware and software to relay programming commands from the central programmer to an implanted device, for relaying diagnostic information and programming acknowledgement signals from the implanted device to the central programmer, and for performing related functions such as error detection and correction functions. In one example, each remote telemetry unit includes a CODEC or other appropriate electronics for interfacing with a telephone line, a telemetry antenna for positioning in proximity to the implanted device, and a digital signal processor (DSP) for processing signals transmitted between the central programmer and the implanted device via the CODEC and antenna. The telemetry unit also includes minimal user interface components, such as simple lights or buzzers for notifying the user that, for example, reliable communications has been established.

The central programmer is installed within a central data collection center or within a physician office, such as the office of a cardiologist supervising the programming of implanted devices within numerous patients. The remote telemetry units are installed within locations permitting ease of access by patients with implanted devices. The telemetry units may be provided within the individual homes of the patients to permit reprogramming of the implanted device under the supervision of the physician without requiring the patient to visit a physician or the physician to visit the patient. Telemetry units are also installed within clinics, mobile or otherwise, as may be found in remote areas not frequently visited by cardiologists or others expert in the programming of implanted devices. Still other telemetry units are installed within hospitals, particularly within emergency rooms, to permit convenient reprogramming of implanted devices in emergency situations, as may be required if operation of the device is triggering an arrhythmia within a patient such as a pacemaker mediated tachycardia (PMT). Telemetry units may be provided within senior citizen homes for use with patients therein having implanted devices. Within hospitals, the telemetry units may also be provided within the individual rooms of patients having implanted devices. Still other telemetry units may be provided within public locations, such as within airports, police stations, or the like to permit convenient reprogramming of devices, again particularly in emergency situations. Still other appropriate locations for the installation of remote telemetry units include any medical facilities within prisons, schools, public transportation facilities, and the like.

In the specific implementation of FIG. 2, the central programmer communicates with the remote telemetry unit via the public switched telephone network (PSTN) or other land line communication link, such as T1 line, ISDN line, or the like. Alternatively, individual telemetry units may be provided for use or in connection with wireless communication devices to permit the central programmer to communicate with the telemetry unit via satellite based wireless communication systems or cellular telephone systems or the like. Preferably, however, communication is provided through a conventional PSTN to reduce the overall cost of the telemetry unit. In still other implementations, the individual telemetry units communicate with the central programmer via the Internet or other interconnected computer network.

Thus, the remote telemetry unit may be installed in a wide variety of locations. As will be described more fully below, the degree of programmability achieved through the remote telemetry unit depends upon the degree of supervision of the patient. Briefly, for telemetry units installed within locations under the control of nurses or other medical professionals, a high degree of programmability is permitted. For remote telemetry units installed within patient homes or other locations wherein no medical professional is available to assist the patient during reprogramming, only limited reprogramming is provided. For telemetry units installed within clinics operated under the supervision of a nurse, an intermediate degree of programmability is permitted. For telemetry units connected directly to the central programmer for use by the physician or other highly trained medical professional, a full and unrestricted range of programmability is provided. Thus, three general tiers of programmability are provided. However, in other implementations, more or fewer tiers or programmability may be employed. Generally, in circumstances wherein the patient is under no direct medical supervision, programming is restricted to only certain functions which may affect diagnostics and other non-"life threatening" functions, such as functions pertaining to the reprogramming of diagnostics, sleep mode, rate responsive programming parameters, and the like. Reprogramming of any parameters which may potentially have significant adverse affects on the health of the patient, such as reprogramming of sensitivity or pacing mode, are preferably restricted to circumstances wherein the patient is under the direct supervision of a nurse or physician who can ensure that the remote telemetry unit is properly used to ensure proper reprogramming of the device and who can respond to any serious medical condition that may occur during or subsequent to reprogramming. As can be appreciated, in circumstances wherein the patient is under no supervision, such as within the home of the patient, the patient may not properly hold the antenna of the telemetry unit in close proximity to the implanted device at all times during the programming session, resulting in incomplete or improper reprogramming of certain functions. Thus, for example, if the sensitivity by which the implanted device detects intrinsic heart signals is incorrectly reprogrammed, the device may then fail to detect a natural sinus rhythm of the heart and instead administer disruptive pacing pulses, perhaps triggering a tachyarrhythmia. Alternatively, the sensitivity may be set such that random electrical noise within the heart is detected and misidentified as sensed beats, although the heart may have stopped beating on its own, resulting in a failure to administer pacing pulses.

Figure 3:
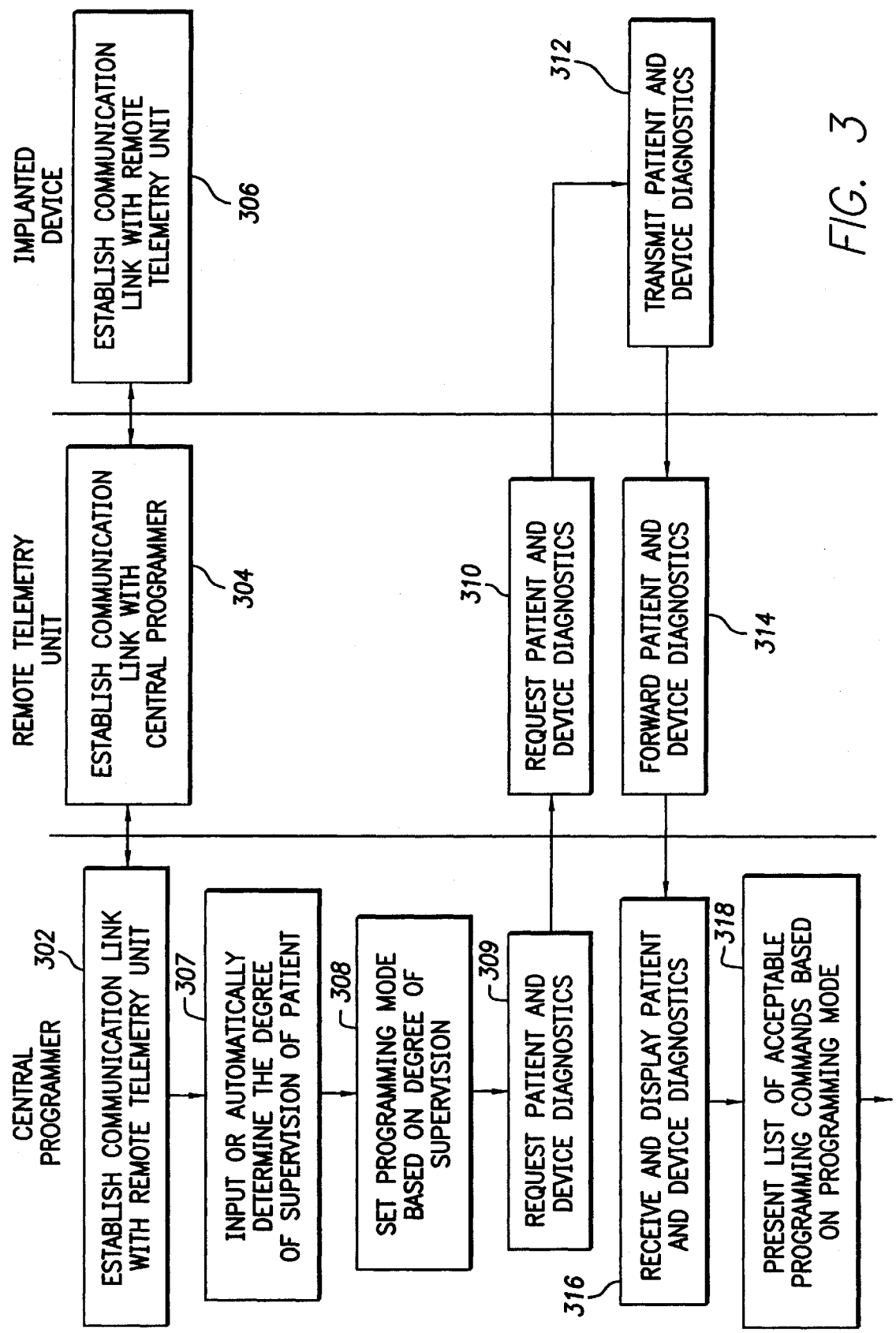
FIG. 3 is a first portion of a flow chart illustrating a sequence of steps performed by the central programmer, remote telemetry unit, and implanted device for use in programming the implanted device using the system of FIG. 2.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

These and other features of the overall system will be described in greater detail with reference to the flow chart of FIG. 3 which provides the sequence of steps performed by the central programmer, the remote telemetry unit, and the implanted device during a typical programming session. Initially, at steps 302 and 304 the central programmer and remote telemetry unit establish a communication link therebetween. Assuming interconnection via the PSTN, the central programmer dials a telephone number associated with the remote telemetry unit, which detects the incoming telephone call and forwards responsive communication handshake signals or other communication protocol signals to the central programmer for establishing a reliable communication link. The quality of the communication link may be automatically determined by transmitting signals at different communication rates between the central programmer and the remote unit to determine the highest data transference rate which can be reliably sustained.

Once communication has been established between the central programmer and the remote unit, the physician, who is simultaneously in contact with the nurse or patient via the telephone, instructs the nurse or patient to place the antenna of the remote unit over the implanted device to thereby permit establishing a communication link between the implanted device and the remote unit, step 306. Additionally, signals are forwarded to the central programmer directly informing the physician that the link has been established. To permit the physician to converse with the patient or nurse via telephone while the central programmer is telephonically connected to the remote programmer, the remote programmer is provided with two telephone jacks, one for connecting the remote programmer to the PSTN and the other for connecting the remote programmer to a telephone. Electronics within the remote programmer detects whether or not the telephone is on-hook or off-hook and, if off-hook, routes voice telephone signals from the physician operating the central programmer to the telephone of the patient to permit the physician to converse with the patient and vice versa. When the Electronics detects the telephone on-hook, the remote programmer routes signals received from the central programmer to the telemetry unit for transmission to the implanted device. In this manner, only a single telephone line is required to permit both telephone conversations between the nurse or patient and the physician and to permit signal transmissions between the central programmer and the remote programmer.

At step 307, the central programmer inputs the degree of supervision of the patient to permit the programmer to set the programming mode, i.e., the degree of programmability at step 308. Depending upon the implementation, the location of the remote telemetry unit may be input directly by the physician from a list of locations such as: "physician-supervised"; "nurse-supervised"; "unsupervised." Alternatively, the location of the remote telemetry unit may be automatically detected subsequent to establishing a communication link with the device. To this end, each remote telemetry unit is provided with an internal serial number or other designation from which the programmer determines the general location of the programmer. Programmers for installation within physician-supervised offices or hospital are provided with serial numbers within a certain range, whereas telemetry units for use in clinics are provided with serial numbers within another range, and telemetry units for use in patient homes are provided with serial numbers within still another range. The central programming unit accesses the serial number of the telemetry unit and determines therefrom the location of the telemetry unit and the mode of programming associated therewith.

At step 309, the central programmer transmits signals to the remote unit requesting that patient and device diagnostics be uploaded from the implanted device. The signals are in turn forwarded to the implanted device from the remote unit at step 310. At step 312 the implanted device responds by transmitting patient and device diagnostics, such as a list of current programming parameters stored therein and any IEGM signals recorded therein or other recorded events. The patient and device diagnostics are forwarded at step 314 from the remote unit to the central programmer for display thereon at step 316. The physician then informs the patient or nurse that the antenna of the remote unit can be temporarily removed from the vicinity of the implanted device while the physician reviews the patient and device diagnostics. Real time IEGM with markers and skin ECG can also be transmitted to the central programmer.

Figure 4:
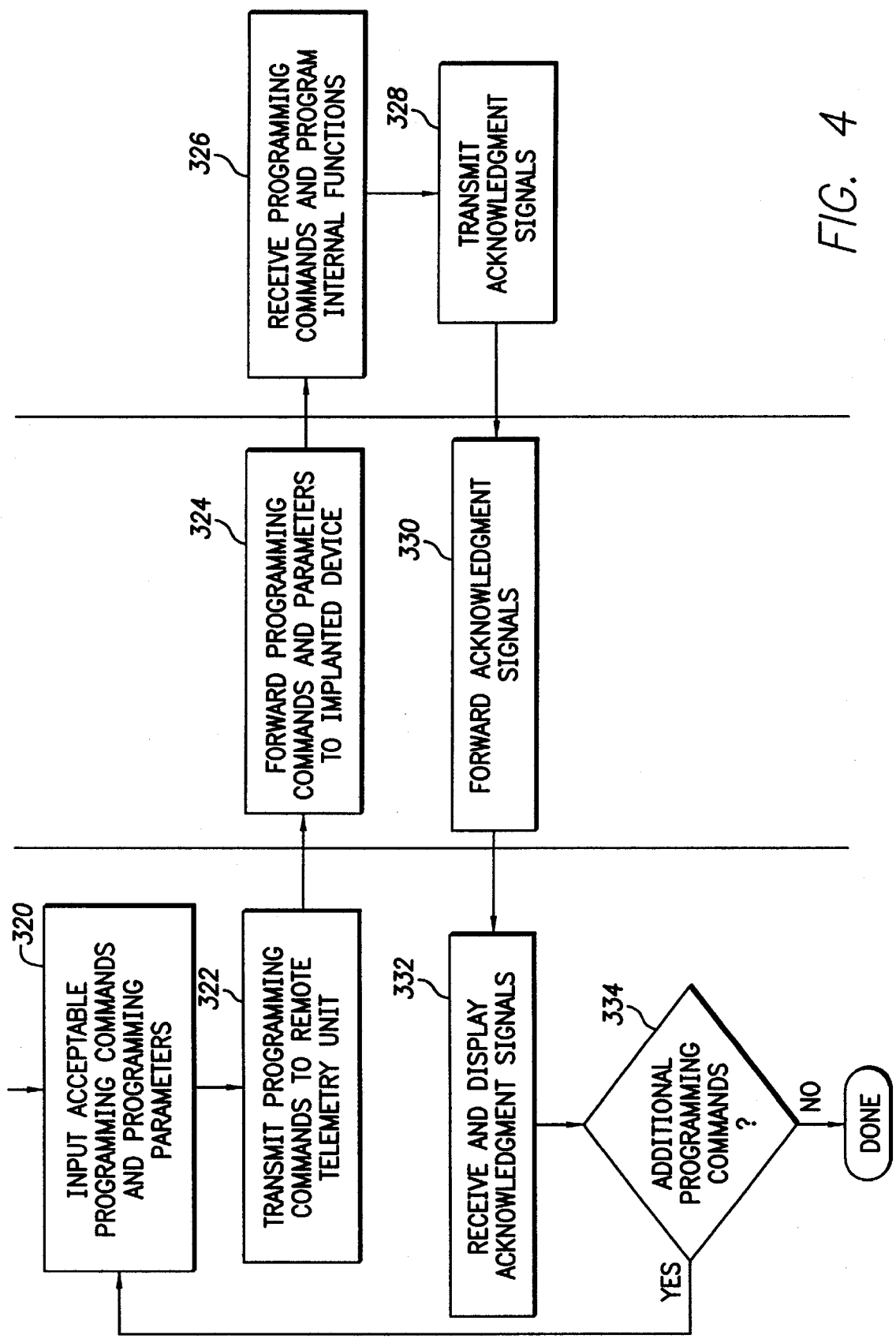
FIG. 4 is a second portion of the flow chart of FIG. 3 illustrating additional steps performed by the central programmer, remote telemetry unit, and implanted device.

After the diagnostics have been reviewed, the physician is presented with a list of acceptable programming commands at step 318 for use in reprogramming the device. The acceptable commands are based upon the particular programming mode previously selected based upon the degree of supervision. Referring now to FIG. 4, beginning at step 320, the physician then inputs selected programming commands and corresponding parameters for use in reprogramming the implanted device. At step 322 the programming commands and parameters are transmitted from the central programming unit to the remote unit which, at step 324, forwards the commands to the implanted device. The programming commands are received by the implanted device at step 326 and used therein to reprogram internal functions of the device. Assuming that the device has been successfully reprogrammed, acknowledgement signals are generated and transmitted from the implanted device at step 328 to the remote unit and forwarded at step 330 to the central programmer for receipt and display at step 332. If additional programming is required as determined at step 334, processing returns to step 320 for input of the additional programming commands. Otherwise, the programming session is completed and the various communication links are disabled and disconnected.

Thus, FIGS. 3 and 4 set forth the basic steps performed by the central programmer, remote unit and implanted device for reprogramming the implanted device based upon commands generated at the central programmer. Within FIGS. 3 and 4, only high level steps are illustrated. Numerous substeps may need to be performed in connection with high level step to implement the step. For example, for each step involving the transmission of signals from one device to another, individual error detection and correction sub-steps are performed and appropriate error or acknowledgement signals are returned to the transmitting device. Also various levels of error detection are performed. On one level, the receiving device verifies that the received signals are not corrupted, as may be achieved using conventional cyclic redundancy check (CRC) bits. Additionally, the receiving device evaluates the programming commands and specific programming values received to verify that the commands are valid and the parameters are within predetermined acceptable ranges of values. For example, if a programming parameter associated with device sensitivity is outside the range of acceptable levels of sensitivity, then an error signal is returned to the transmitting device. As can be appreciated, a wide variety of error detection techniques may be employed depending upon the particular parameters being reprogrammed and no attempt is made herein to provide an exhaustive list. Error detection and correction techniques may depend upon the particular communication medium employed and hence may differ depending upon whether, for example, land line or wireless communication protocols are employed.

Figure 5:
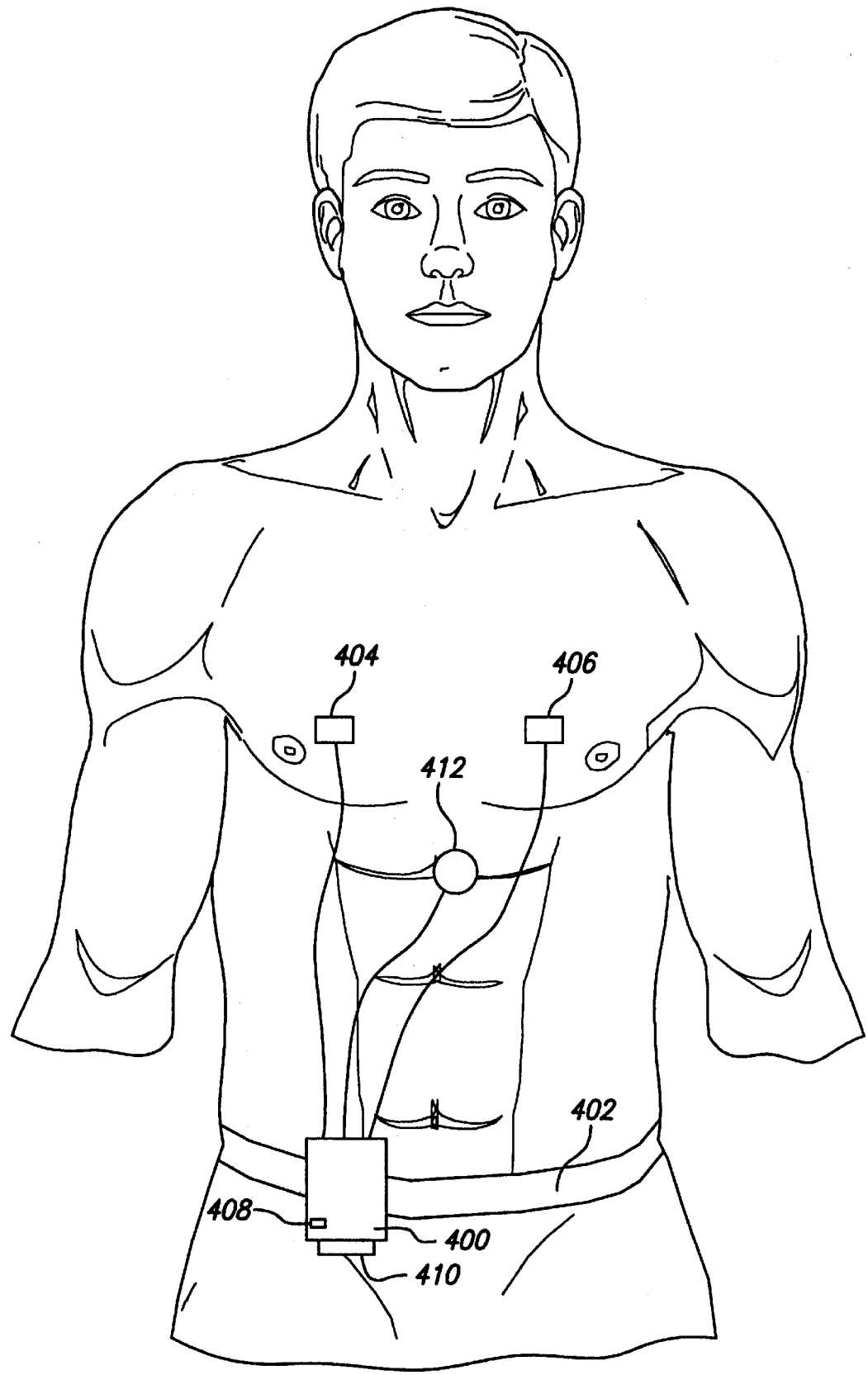
FIG. 5 illustrates an alternative implementation of the remote telemetry unit of FIG. 2 wherein the remote unit is configured to also function as a Holter monitor.

FIG. 5 illustrates an alternative implementation wherein the remote programming device additionally serves as a Holter monitor for detecting and recording electrocardiogram (ECG) data or other data from the patient. The remote programming device 400 is provided with a belt 402 for attaching the device to the waist of the patient. A pair of electrodes 404 and 406 adhesively attach to the chest of the patient to permit ECG signals to be detected and recorded within the remote programming device. Preferably, the device is provided with sufficient memory to store 24 to 48 hours of ECG recordings for later analysis by a physician. In use, the physician instructs the patient over the telephone to attach the electrodes to the chest and to activate the remote device to record the ECG for a predetermined period of time. Upon completion of the period of time, the patient is instructed to remove the remote programming device from the belt and to connect the device via a telephone jack 408 to a telephone line such that the physician may download the recorded ECG signals via the telephone line into the central programmer. To automate the collection of data from the Holter monitor, an automated telephonic system may be provided whereby the patient manually dials or the transmitter automatically dials the automated system and responds to various pre-recorded instructions provided therewith. The instructions provide information to the patient on how to collect the data and how to transmit the data for analysis. Preferably, the automated system receives ECG and other data transmitted from the Holter monitor for automated analysis or for forwarding to the physician. In this manner, the physician or other medical professional need not directly converse with each patient whenever data is to be collected or transmitted, thereby minimizing overall costs. Alternatively, the memory of the remote programming device may be configured as a removable memory module 410, which the patient merely returns to a medical clinic or to the physician. An advantage of providing a memory module is that software for use by the remote programming device may thereby be easily upgraded by simply providing a new module.

Additionally, a telemetry unit 412 is provided to permit the remote device to receive diagnostic data from the implanted device for storage along with the ECG data in the memory module or other memory device of the remote unit. The diagnostic data may include, for example, IEGM data detected internally by the implanted device. Telemetry unit 412 also permits the remote device to act as a remote programmer for communicating programming signals between the central programming device and the implanted device. Preferably, reprogramming of the implanted device is performed with the remote programming device detached from the waist of the patient. The remote device is positioned on a table, adjacent to the patient; the patient connects the telephone line into the telephone jack; and then positions the telemetry unit over the implanted device. Reprogramming signals are transmitted from a central programmer to the remote device and then via the telemetry unit into the implanted device. Diagnostic information received from the implanted device is routed to the central programmer. Depending upon the implementation, previously-detected or concurrently-detected ECG data may be transmitted to the central programmer along with the diagnostic data from the implanted device. As with the embodiments discussed above, the telephone line is preferably routed through the telephone of the patient permitting the patient to converse with the physician before and after transmission of reprogramming signals.

Thus FIG. 5 illustrates an embodiment wherein the remote programming device serves both as a remote programmer for reprogramming the implanted device and as a Holter monitor or similar device for detecting and recording large quantities of ECG information or other data.

What has been described are various programming systems for use with implantable cardiac stimulation devices. The various functional components of the exemplary systems may be implemented using any appropriate technology including, for example, microprocessors running software programs or application specific integrated circuits (ASICs) executing hard-wired logic operations. Although described primarily with respect to a pacemaker, aspects of the invention are applicable to other implantable cardiac stimulation devices, such as ICDs. The exemplary embodiments of the invention described herein are merely illustrative of the invention and should not be construed as limiting the scope of the invention.

What is claimed is:

1. A system for remote programming of an implantable cardiac stimulation device, the system comprising:

a central programmer device operative to generate and transmit programming signals for use in programming a stimulation device implanted within a patient;

a remote programmer device, for use in proximity to the patient, operative to receive and relay the programming signals transmitted by the central programmer device to the implantable cardiac stimulation device of the patient for programming the stimulation device with the programming signals; and wherein the remote programmer device includes a Holter monitor operative to monitor and record surface electrocardiogram (ECG) signals.

2. A system for remotely programming a plurality of implantable cardiac stimulation devices, the system comprising:

a central programmer device operative to generate and transmit programming signals for use in programming selected ones of a plurality of implantable cardiac stimulation devices implanted within respective patients;

a plurality of remote programmer devices each for use with a respective one of the patients and operative to receive and relay the programming signals generated by the central programmer device to the implantable cardiac stimulation device of the respective patient; and with the central programmer device also being operative to input an indication of a degree of direct medical supervision of the respective patient during programming of the implanted device of the respective patient and to control the generation of programming signals based upon the degree of direct medical supervision.

3. A system for remote programming of an implantable cardiac stimulation device implanted within a patient, the system comprising:

a central programmer device operative to generate programming signals for use in programming a device implanted within a patient who is at a location remote from the local programmer device;

a remote programmer device, for use in proximity to the patient, operative to receive the signals from the central programmer device and to relay the programming signals to the stimulation device to program the stimulation device; and a network system, coupled between the central programmer device and the remote programmer device, that controls communication therebetween.

4. A system for remote programming of an implantable cardiac stimulation device implanted within a patient, the system comprising:

means for locally generating a set of programming parameters for use in programming the implantable cardiac stimulation device;

means for transmitting the set of programming parameters via a computer network; and means, for use in proximity to the patient, for receiving the programming parameters from the computer network and for relaying the programming parameters to the stimulation device to program the device.

5. A system for remote programming of an implantable cardiac stimulation device implanted within a patient, the system comprising:

means for locally inputting an indication of a degree of direct medical supervision of the patient during programming of the implanted device;

means for locally generating a set of programming parameters for use in programming the implantable cardiac stimulation device, with the programming parameters varying depending upon the degree of direct medical supervision of the patient;

means for transmitting the set of programming parameters; and means, for use in proximity to the patient, for receiving and relaying the programming parameters to the implantable cardiac stimulation device to program the device.

6. The system of claim 5, wherein the means for transmitting the set of programming parameters includes means for transmitting via one or more of a telephone land line, a wireless communication system, a local computer network, and the Internet.

7. The system of claim 5, wherein the means for receiving and relaying the programming parameters to the implantable cardiac stimulation device includes a Holter monitor for monitoring and recording surface electrocardiogram (ECG) signals.

8. A method for remote programming of an implantable cardiac stimulation device implanted within a patient using a central programmer device for generating programming signals and a remote programmer device for use in proximity to a patient for relaying programming signals to the implanted device, the method comprising the steps of:

inputting into the central programmer device an indication of a degree of direct medical supervision of the patient during programming of the implanted device;

controlling the central programmer device to generate programming signals for use in programming the implanted device, with the generation of the programming signals controlled based upon the indicated degree of direct medical supervision of the patient;

transmitting the programming signals to the remote programmer device; and relaying the programming signals from the remote programmer device to the implanted device for programming of the device with the programming signals.

9. The method of claim 8, wherein the indication of the degree of direct medical supervision input to the central programmer device specifies either supervised or unsupervised.

10. The method of claim 9, wherein the implanted device accepts a set of programming commands and wherein, if the indication of the degree of direct medical supervision specifies an unsupervised patient, the central programmer device is controlled to generate programming signals pertaining to only a predetermined subset of the programming commands.

11. The method of claim 10, wherein if the indication of the degree of direct medical supervision specifies a supervised patient, the central programmer generates programming signals pertaining to only the set of programming commands accepted by the implanted device.

12. The method of claim 10, wherein for a particular programming command, the implanted device accepts a range of programming values, and wherein if the indication of the degree of direct medical supervision specifies an unsupervised patient, the central programmer device is controlled to generate programming signals for the particular programming command pertaining to only a predetermined subset of programming values from within the range of programming values accepted by the implanted device.

13. A system for remote programming of an implantable cardiac stimulation device implanted within a patient, the system comprising:

a central programmer device operative to generate and transmit programming signals for use in programming a stimulation device implanted within a patient, with the programming signals generated based, in part, upon a degree of direct medical supervision of the patient during programming of the device; and a remote programmer device, for use in proximity to the patient, operative to receive and relay the programming signals transmitted by the central programmer device to the stimulation device of the patient to program the stimulation device with the programming signals.

14. The system of claim 13, wherein the central programmer device is operative to input an indication of the degree of direct medical supervision input which specifies either unsupervised, nurse-supervised or physician-supervised.

15. The system of claim 13, wherein the implantable cardiac stimulation device is a pacemaker or an implantable cardioverter defibrillator.

16. The system of claim 13, wherein the central programming device and the remote programming device both include the communication units for communicating with one another via a communication channel.

17. The system of claim 16, wherein the communication channel includes one or more of a telephone land line, a wireless communication channel, and the Internet.

18. The system of claim 16, wherein the communication units of the central programming device and the remote programming device both include error detection and correction circuits operative to detect and correct communication errors therebetween.

19. The system of claim 16, wherein the communication units of the central programming device and the remote programming device include secure communication protocol circuits for ensuring a secure communication link.

20. The system of claim 13, wherein the remote programmer device includes a Holter monitor for monitoring and recording surface electrocardiogram (ECG) signals.

21. The system of claim 20, wherein the remote programmer device additionally includes a modular memory unit for recording the surface ECG signals.

22. The system of claim 21, wherein the modular memory unit also stores control software for controlling the operations of the remote programmer device such that the control software is upgradable by providing a new modular memory unit to accommodate new or modified implantable cardiac stimulation devices.

23. The system of claim 13, wherein the central programmer device is operative to input an indication of the degree of direct medical supervision input which specifies either supervised or unsupervised.

24. The system of claim 23, wherein the implanted device accepts a set of programming commands, and wherein if the indication of the degree of direct medical supervision specifies an unsupervised patient, the central programmer generates programming signals pertaining to only a predetermined subset of the programming commands.

25. The system of claim 24, wherein programming commands not within the predetermined subset of programming commands include pacing mode programming commands and sensitivity programming commands.

26. The system of claim 24, wherein if the indication of the degree of direct medical supervision specifies a supervised patient, the central programmer generates programming signals pertaining to any of the set of programming commands accepted by the implanted device.

27. The system of claim 24, wherein the predetermined subset of programming commands include nonlife-threatening programming commands.

28. The system of claim 27, wherein the nonlife-threatening programming commands include diagnostic mode programming commands, sleep mode programming commands, and rate responsive mode programming commands.

29. The system of claim 24, wherein for a particular programming command, the implanted device accepts a range of programming values and wherein if the indication of the degree of direct medical supervision specifies an unsupervised patient, the central programmer generates programming signals for the particular programming command pertaining to only a predetermined subset of programming values from with the range of programming values accepted by the implanted device.

30. The system of claim 29, wherein the programming values for the particular programming command specify a voltage and wherein the predetermined range of programming values specifies a range of voltages narrower than the range of voltage values accepted by the implanted device.

31. The system of claim 29, wherein the programming values for the particular programming command specify timing values and wherein the predetermined range of programming values specifies a range of timing values narrower than the range of timing values accepted by the implanted device.

32. The system of claim 29, wherein if the indication of the degree of direct medical supervision specifies a supervised patient, the central programmer generates programming signals pertaining to only the range of programming values accepted by the implanted device.

* * * * *